US011219598B2

(12) United States Patent
Yasukawa (10) Patent No.: US 11,219,598 B2
(45) Date of Patent: Jan. 11, 2022

(54) OPHTHALMIC DRUG SUSTAINED RELEASE DEVICE (71) Applicant: PUBLIC UNIVERSITY CORPORATION NAGOYA CITY UNIVERSITY, Nagoya (JP)

(72) Inventor: Tsutomu Yasukawa, Nagoya (JP)

(73) Assignee: PUBLIC UNIVERSITY CORPORATION NAGOYA CITY UNIVERSITY, Nagoya (JP)

(*) Notice: Subject to any disclaimer, the term of this patent is extended or adjusted under 35 U.S.C. 154(b) by 102 days.

(21) Appl. No.: 16/094,506

(22) PCT Filed: Apr. 19, 2017

(86) PCT No.: PCT/JP2017/015783
§ 371 (c)(1),
(2) Date: Oct. 18, 2018

(87) PCT Pub. No.: WO2017/191759
PCT Pub. Date: Nov. 9, 2017

(65) Prior Publication Data
US 2019/0099366 A1    Apr. 4, 2019

(30) Foreign Application Priority Data

May 6, 2016 (JP) .............................. JP2016-093496

(51) Int. Cl.
*A61K 9/00* (2006.01)
*A61F 9/007* (2006.01)
*A61M 31/00* (2006.01)

(52) U.S. Cl.
CPC ............ *A61K 9/0051* (2013.01); *A61F 9/007* (2013.01); *A61K 9/00* (2013.01); *A61M 31/002* (2013.01)

(58) Field of Classification Search
None
See application file for complete search history.

(56) References Cited

U.S. PATENT DOCUMENTS

2012/0035528 A1* 2/2012 Coppeta ............... A61K 9/0009
604/20
2013/0261535 A1* 10/2013 Behar-Cohen ....... A61K 49/223
604/22

FOREIGN PATENT DOCUMENTS

| JP | 2004-536631 A | 12/2004 |
|----|---------------|---------|
| JP | 2006-516619 A | 7/2006  |
| JP | 2009-535083 A | 10/2009 |

(Continued)

OTHER PUBLICATIONS

Wong (The Ophthalmology Examinations Review; World Scientific Publishing Company 2001 p. 162) 1 page (Year: 2001).*

(Continued)

*Primary Examiner* — Ernst V Arnold
(74) *Attorney, Agent, or Firm* — Locke Lord LLP (57) ABSTRACT

An object of the present invention is to provide a sustained drug release system useful for treating eye diseases. There is provided a device for sustained release of an ophthalmic drug, comprising a drug enclosing part and an intraocular retention gas enclosing part adjacent to the drug enclosing part, the enclosing parts being provided in a hollow container having at least one opening part, wherein the drug enclosing part is isolated from the opening part by the intervention of the intraocular retention gas enclosing part.

19 Claims, 8 Drawing Sheets

(56) References Cited

FOREIGN PATENT DOCUMENTS

| | | |
|---|---|---|
| WO | 2002089767 A1 | 11/2002 |
| WO | 2004066980 A1 | 8/2004 |
| WO | 2007125456 A1 | 11/2007 |
| WO | 2011097634 A1 | 8/2011 |

OTHER PUBLICATIONS

Supplemental European Search Report dated Dec. 10, 2019, issued for the European Patent Application No. 17792692.0.
International Search Report dated Jun. 27, 2017, issued for PCT/JP2017/015783.

* cited by examiner

OPHTHALMIC DRUG SUSTAINED RELEASE DEVICE

TECHNICAL FIELD

The present invention relates to a sustained drug release system. In particular, the invention relates to a device for sustained release of an ophthalmic drug and uses thereof. The present application claims priority based on Japanese Patent Application No. 2016-093496 filed on May 6, 2016, the entire contents of which are incorporated herein by reference.

BACKGROUND ART

Drug delivery systems are used for the purpose of increasing therapeutic effects and reducing side effects. Drug delivery systems are roughly divided into those for (1) drug release control (controlled release), (2) drug targeting (targeting), and (3) absorption promotion (transdermal absorption/gene introduction, etc.). In the field of ophthalmology, development of drug delivery systems for (1) is vigorously carried out. For example, Vitrasert (registered trademark) (FDA approved) (sustained release of ganciclovir against cytomegalovirus retinitis (AIDS)), Retisert (registered trademark) (FDA approved) (sustained release of fluocinolone acetonide against non-infectious uveitis), Iluvien (registered trademark) (FDA approved) (sustained release of fluocinolone acetonide against diabetic macular edema), I-vation™ (under overseas trial) (sustained release of triamcinolone/acetonide against diabetic macular edema), and NT-0501 (under overseas Phase II study) (sustained release of CNTF against retinitis pigmentosa and atrophic age-related macular degeneration) as non-degradable implants (reservoir type), Ozurdex (registered trademark) (FDA approved) (sustained release of dexamethasone against macular edema) as a biodegradable implant (monolithic type), DE-102 (sustained release of betamethasone against diabetic macular edema) as microspheres (monolithic type), and the like have been developed.

On the other hand, in recent years, development of molecular target therapeutic drugs has progressed, antibody drugs (e.g., bevacizumab, ranibizumab), genetically modified fused glycoprotein preparations (e.g., aflibercept), and aptamer preparations (e.g., pegaputanib) have been developed, and good treatment results for exudative age-related macular degeneration, macular edema associated with diabetic retinopathy and retinal vein occlusion and myopic choroidal neovascularization have been reported.

Examples of sustained drug release devices are presented in Patent Literatures 1 and 2. Patent Literature 1 discloses an implantable micropump that releases a drug by the generated gas pressure. On the other hand, Patent Literature 2 discloses an intraocular sustained release device that releases a drug by diffusion.

CITATION LIST

Patent Literature

Patent Literature 1: Japanese Translation of PCT International Application Publication No. 2009-535083 A Patent Literature 2: Japanese Translation of PCT International Application Publication No. 2006-516619 A

SUMMARY OF INVENTION

Technical Problem

Protein/peptide preparations represented by antibody drugs are highly specific, and are expected to be used and applied more and more in the future. However, the duration after administration is not long and continuous administration (typically monthly administration) is required to maintain efficacy. Also, since such preparations are normally administered at a high concentration, side effects are concerned. On the other hand, in conventional sustained drug release control (controlled release) technologies, it is difficult to prepare sustained release protein/peptide preparations such as antibodies and cytokines for reasons such as their water solubility and high molecular weight, and easy deactivation in processes such as heat treatment. The present invention aims at solving these problems.

Solution to Problem

As a result of intensive studies to solve the above problems, the present inventors have arrived at the following invention.

A device for sustained release of an ophthalmic drug, comprising a drug enclosing part and an intraocular retention gas enclosing part adjacent to the drug enclosing part, the enclosing parts being provided in a hollow container having at least one opening part, wherein the drug enclosing part is isolated from the opening part by the intervention of the intraocular retention gas enclosing part.

When the device for sustained release of an ophthalmic drug is transplanted intraocularly or extraocularly, the intraocular fluid flows into the container through the opening part. The inflowing intraocular fluid dissolves the intraocular retention gas and the residual amount of the intraocular retention gas gradually decreases. When the isolation by the intraocular retention gas is then released (the sealing effect disappears) and the intraocular fluid reaches the drug enclosing part, the drug enclosed in the drug enclosing part dissolves and diffuses to be released to the outside of the container. Briefly, the drug is sustainedly released. Thus, according to the present invention, the drug can be sustainedly released (drug efficacy can be maintained) over a long period of time despite a simple configuration. As a result, the dose and administration frequency of the drug are suppressed so that the problem of side effects can be solved. Also, it is possible to contribute to the medical economy. Furthermore, since the drug can be enclosed in a solid state, deterioration of the drug at the time of storage is prevented and a preparation excellent in storage stability is obtained. On the other hand, the device has a simple structure and thus is relatively easily manufactured. In addition, since it is possible to separate the process for manufacturing the container which constitutes the device from the drug enclosing process, there is no need to prepare a container for each drug. Briefly, sustained release of various drugs becomes possible with one type of container.

BRIEF DESCRIPTION OF DRAWINGS

FIGS. 1(A)-(H) show examples of a sustained release device. FIG. 1(A): One cavity type; FIG. 1(B): serial multi-chamber type; FIG. 1(C): two-chamber type; FIG. 1(D): serial multi-chamber type; FIG. 1(E): parallel multi-chamber type (pipe organ type); FIG. 1(F): serial tubular type;

FIG. 1(G): serial tubular type; and FIG. 1(H): as-necessary opening compartment type (arrows represent opening parts by a YAG laser or the like).

FIGS. 3(A) and (B) show the construction of a hollow device made of a polymethyl methacrylate (PMMA) resin (FIG. 3(A)) and the injection of a drug and an intraocular retention gas FIG. 3(B).

FIGS. 5(A) and (B) show an amount of a gas remaining in the PMMA hollow device after transplantation into a rabbit (FIG. 5(A)) and a drug release profile (FIG. 5(B)).

FIGS. 6(A) and (B) show another example of the sustained release device. (a) There are shown states in which a sustained release device 10 is observed from the front (FIG. 6(A)) and the side (FIG. 6(B)). (b) There is shown a state in which the sustained release device 10 is observed obliquely.

DESCRIPTION OF EMBODIMENTS

The present invention relates to a device for sustained release of an ophthalmic drug (hereinafter abbreviated as "sustained release device"). The sustained release device of the present invention is ophthalmic, i.e., is applied to eye diseases. Examples of diseases to which the sustained release device of the present invention can be applied (i.e., diseases which can be treated or prevented by using the present invention) include vitreoretinal diseases such as age-related macular degeneration, chorioretinal atrophy, macular edema (associated with diabetic retinopathy, retinal vein occlusion, and uveitis), retinitis pigmentosa, macular dystrophy, macular telangiectasia types 1 and 2, retinal detachment, proliferative vitreoretinopathy, proliferative diabetic retinopathy, familial exudative vitreoretinopathy, retinoblastoma, Coat's disease and uveitis, glaucoma, neovascular glaucoma, optic neuropathy, malignant melanoma, and malignant lymphoma. In order to exhibit its characteristic sustained release effect, the sustained release device of the present invention has the following configuration. First, in a hollow container having at least one opening part, a drug enclosing part and an intraocular retention gas enclosing part adjacent thereto are provided. The drug enclosing part is isolated from the opening part of the container by the intervention of the intraocular retention gas enclosing part. Preferably, in order to enhance the sustained release effect, a plurality of units each including a drug enclosing part and an ocular retention gas enclosing part adjacent to the drug enclosing part are provided. In this case, the distance from the opening part of the container to the drug enclosing part is different among the units, and the intraocular retention gas enclosing part of each of the units communicates with the opening part of the container directly or via any other unit. In this way, if a plurality of units are provided and the distance from the opening part to the drug enclosing part is configured to be different among the units, the sustained release action occurs at a plurality of timings, so that the sustained release of the drug over a longer period of time becomes possible.

In one embodiment, the inside of the container is in a porous state (porous body) in which a plurality of drug enclosing parts and a plurality of intraocular retention gas enclosing parts coexist. For example, by freeze-drying a drug solution injected into the container, it is possible to form such a porous state (the drugs in a dry state as the drug enclosing parts are scattered and gaps among the drugs are filled with voids as the intraocular retention gas enclosing parts). In the porous body, the drug enclosing parts in a portion facing the opening part of the container may not be isolated from the opening part by the intraocular retention gas enclosing parts, but an isolation state is formed in a large number of the drug enclosing parts except the drug enclosing parts, and thus the sustained release effect can be obtained based on the above principle. As can be understood from this explanation, it is not essential that the drug enclosing part and the intraocular retention gas enclosing part are completely separated from each other in order to exert its unique action and effect, in the present invention.

The configuration of the present invention will be described in detail with reference to the drawings. FIGS. 1(A)-(H) show specific examples (sustained release devices 1 to 8) in the case where a plurality of units are provided. Their cross sectional shapes are shown so that the internal structure can be seen. Each of the sustained release devices is generally composed of a hollow container, and a drug enclosing part and an intraocular gas enclosing part which are formed inside the hollow container. A plurality of drug enclosing parts and a plurality of intraocular gas enclosing parts are provided. The material for the container is not particularly limited so long as it is low in permeability of the intraocular retention gas to be used and high in biocompatibility. Preferably, a material that does not substantially permeate the intraocular retention gas to be used is adopted. Examples of the material for the container include acrylic resins (for example, polymethyl methacrylate (PMMA) and soft acryl) used for intraocular lenses, contact lenses, medical materials that can be placed in the body and the like; glasses used in optical fibers and the like; and metals such as Ti, Ti alloys and Ni alloys used in implants and the like.

An opening part c is formed in the container. In the illustrated examples, one opening part is provided, but two or more (e.g., 2 to 5) opening parts may be provided. Further, the shape, size and the like of the opening part may be designed in consideration of the sustained release effect. An opening part (hole) for promoting elution of the drug may be provided separately from the portion for introducing the gas.

A drug (therapeutic drug or prophylactic drug) is enclosed in the drug enclosing part. Both water-soluble and lipo-soluble drugs can be used, but the action and effect peculiar to the present invention become remarkable when a water-soluble drug is adopted. In other words, the present invention enables sustained release of a water-soluble drug over a long period of time, which has been difficult with conventional techniques. Specific examples of drugs that can be enclosed in the drug enclosing part include vascular endothelial growth factor (VEGF) inhibitors such as bevacizumab, ranibizumab, aflibercept and pegaptanib, other antibody preparations, aptamer preparations, solubilized receptor preparations, and physiologically active substances such as cytokines. The drug is enclosed in a liquid or solid form. Substrates, additives, and the like used in the preparation of the drug are not particularly limited. That is, for example, oils and fats such as olive oil and silicone oil for suppressing the permeation of moisture in the gas, biodegradable polymers such as polylactic acid and polyglycolic acid and polymers thereof, additives such as vitamin C for suppressing degradation and denaturation of the drug, etc., can be those normally used in the field of ophthalmology, drug adjustment, etc.

An intraocular retention gas is enclosed in the intraocular retention gas enclosing part. The intraocular retention gas is not particularly limited, and sulfur hexafluoride ($SF_6$), propane octafluoride ($C_3F_8$) or the like which has been used in the field of ophthalmology, or air can be used.

Figure 1:
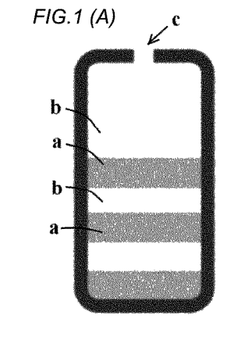

As shown in the drawing, one drug enclosing part and an intraocular retention gas enclosing part adjacent thereto (for example, a drug enclosing part a and an intraocular retention gas enclosing part b in the sustained release device FIG. 1(A) constitute a pair and form one unit. A plurality of units are provided in the container. The number of units is not particularly limited. For example, the number of units can be set within the range of 2 to 30. However, if the number of units is too small, the effect of the present invention, i.e., gradual and long-term sustained release is hardly exerted. If the number of units is too large, for example, the advantage of a simple configuration is impaired. So, the number of units is preferably 3 to 20, more preferably 3 to 15. The plurality of units are provided in series along a direction away from the opening part c of the container, for example, as with the sustained release devices FIG. 1(A) to FIG. 1(D). As with the sustained release devices FIG. 1(B) and FIG. 1(D), partial partition walls w may be provided to partition the respective units. This configuration enables more reliable gradual release of the drug. By providing a tubular part d like the sustained release device FIG. 1(C), it is possible to change the distance from the opening part c to the unit closest to the opening part c, and to adjust the time required to start sustained release. If the volume of the intraocular retention gas enclosing part is designed to be different among the units, gradual and long-term sustained release can be achieved by utilizing the difference in remaining time of the intraocular retention gas. An example employing this configuration is a sustained release device FIG. 1(E).

The shape of the container is not particularly limited, and the container may be formed into a tube, as with sustained release devices FIG. 1(F) and FIG. 1(G). In the sustained release devices FIG. 1(F) and FIG. 1(G), a plurality of units (a pair of drug enclosing part a and intraocular retention gas enclosing part b) are provided so as to be arranged in series along the longitudinal direction of the tubular structure.

In the sustained release devices FIG. 1(A) to FIG. 1(G), an opening part is previously provided in the container, but an opening part may be formed after transplantation. That is, according to a second aspect, the present invention provides a device for sustained release of an ophthalmic drug, comprising a plurality of units each comprising a drug enclosing part and an intraocular retention gas enclosing part adjacent thereto, the units being provided in a hollow container, wherein the plurality of units are partitioned by partition walls, and wherein a region in which an opening part is to be formed after transplantation is provided in an outer wall part of the intraocular retention gas enclosing part of each of the units.

In an example of the sustained release device (sustained release device FIG. 1(H), an opening part c is formed in an outer wall part of the intraocular retention gas enclosing part b in each of the units by a YAG laser, a dye laser, a diode laser, or the like after transplantation. By adopting this configuration, it is possible to release the drug as necessary. Further, since a plurality of units are provided, it is possible to release the drug separately in plural times. That is, gradual and long-term sustained release becomes possible. Typically, one unit is used for a single opening operation, but an opening part may be formed for a plurality of units simultaneously or without providing any substantial time lag.

Figure 6:
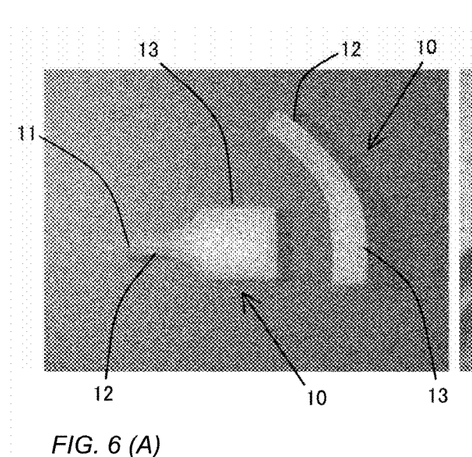

Another example of the sustained release device is shown in FIGS. 6(A) and (B). The sustained release device 10 in FIGS. 6(A) and (B) is composed of a container including a tubular part 12 having an opening part 11 at a tip thereof and a hollow main body part 13 connected thereto, the tubular part 12 and the hollow main body part 13 being integrally formed. The container is filled with a drug in a freeze-dried state (porous and in a state in which gaps among the dried drugs are filled with voids). The drug is filled in a part or all of the main body part 13, all of the main body part 13 and a part of the tubular part 12, or all of the main body part 13 and all of the tubular part 12.

The sustained release device of the present invention is used by being transplanted intraocularly or extraocularly. Specifically, for example, the device is transplanted by any of the following transplantation methods (a) to (d). The transplantation method (b) is adopted in Vitrasert (registered trademark) and Retisert (registered trademark), the transplantation method (c) is adopted in Ozurdex (registered trademark) and Iluvien (registered trademark), and the transplantation method (d) is adopted in Ahmed (registered trademark) Glaucoma Valve, Baerveldt (registered trademark) Glaucoma Implant, or buckling of retinal detachment surgery.

Figure 2:
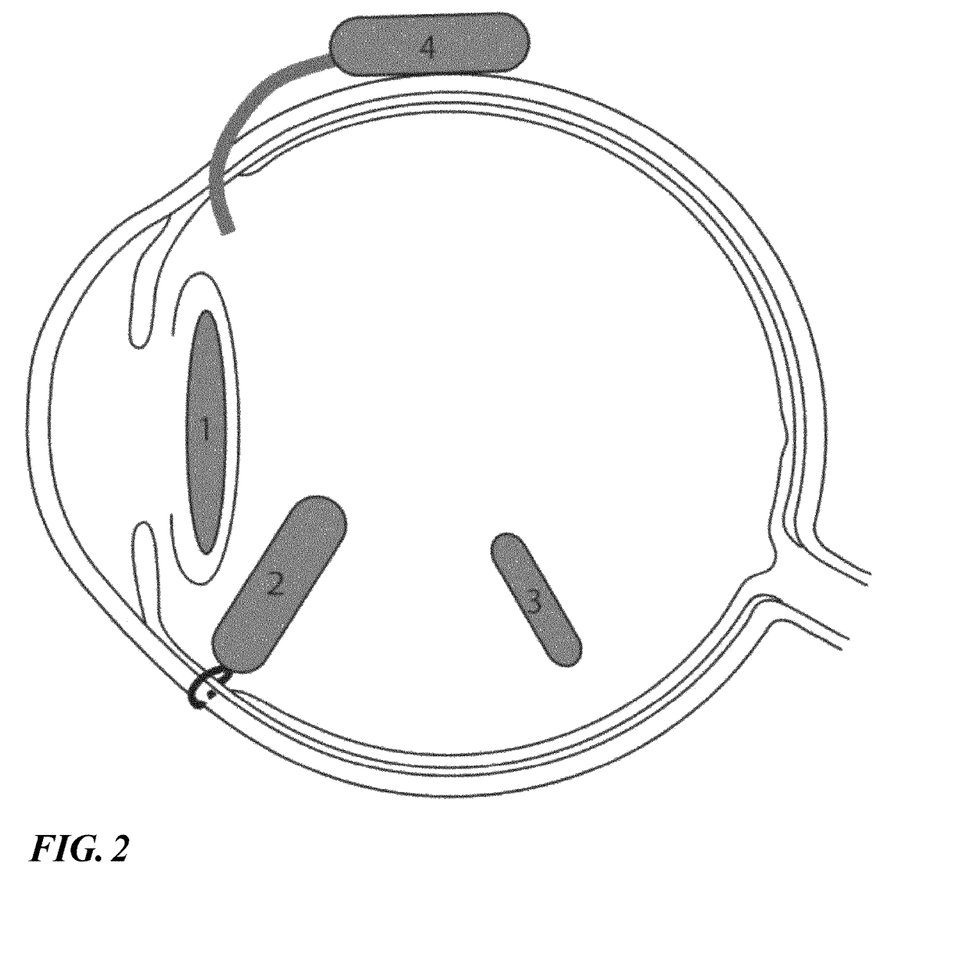
FIG. 2 shows an example of a transplantation site. 1: Fixed in a lens capsular bag or ciliary sulcus, like an intraocular lens; 2: fixed at the pars plana ciliaris; 3: intraocularly inserted; and 4: extraocularly fixed.

(a) Insertion into a lens capsular bag or fixation in a ciliary sulcus (1 in FIG. 2)
(b) intraocular implantation and fixation at the pars plana ciliaris (2 in FIG. 2)
(c) intraocular insertion (3 in FIG. 2)
(d) extraocular implantation (4 in FIG. 2)

The transplantation method (a) is suitable, for example, for treatment of persons of 60 years and over such as those suffering from cataract concurrently, and advantageously provides simple and safe transplantation and enables formation of the opening part in the device by a YAG laser or the like as necessary. The transplantation method (b) is suitable, for example, for treatment of relatively young people, and has an advantage that the method can be conveniently performed as treatment of a disease that can be expected to be cured by a single sustained release. The transplantation method (c) is suitable, for example, for treatment of a disease that can be expected to be cured by a single sustained release and treatment in which vitreous surgery can be administered at a later date, and has an advantage that transplantation is minimally invasive and easy. The transplantation method (d) is suitable, for example, for treatment of chronic diseases that need to be continuously treated for a long period of time, and has advantages that it is easy to remove the device at the time of occurrence of side effects and that it is possible to reload the drug in the device.

EXAMPLES

A. Examination 1 of Effectiveness of Sustained Drug Release System

In order to examine the effectiveness of a sustained drug release system using an intraocular retention gas, the following experiment was conducted. In order to facilitate evaluation of the effect of sealing and sustained release by the intraocular retention gas, a device (hollow device) including one unit composed of a drug enclosing part and an intraocular retention gas enclosing part was made by way of trial to investigate its properties.

1. Preparation of Hollow Device

In order to prepare a hollow device made of a polymethyl methacrylate (PMMA) resin as an acrylic resin having low oxygen permeability, outer edge portions of optical parts of two PMMA intraocular lenses were bonded with an adhesive, as a trial model. The cavity volume was calculated to be 11.3 μL. One opening part was made without using an adhesive (arrow) (FIG. 3(A), and FIG. 4).

2. Enclosure of Solid Drug

Figure 3:
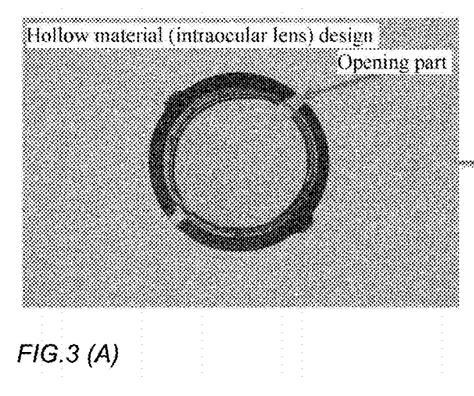
Figure 4:
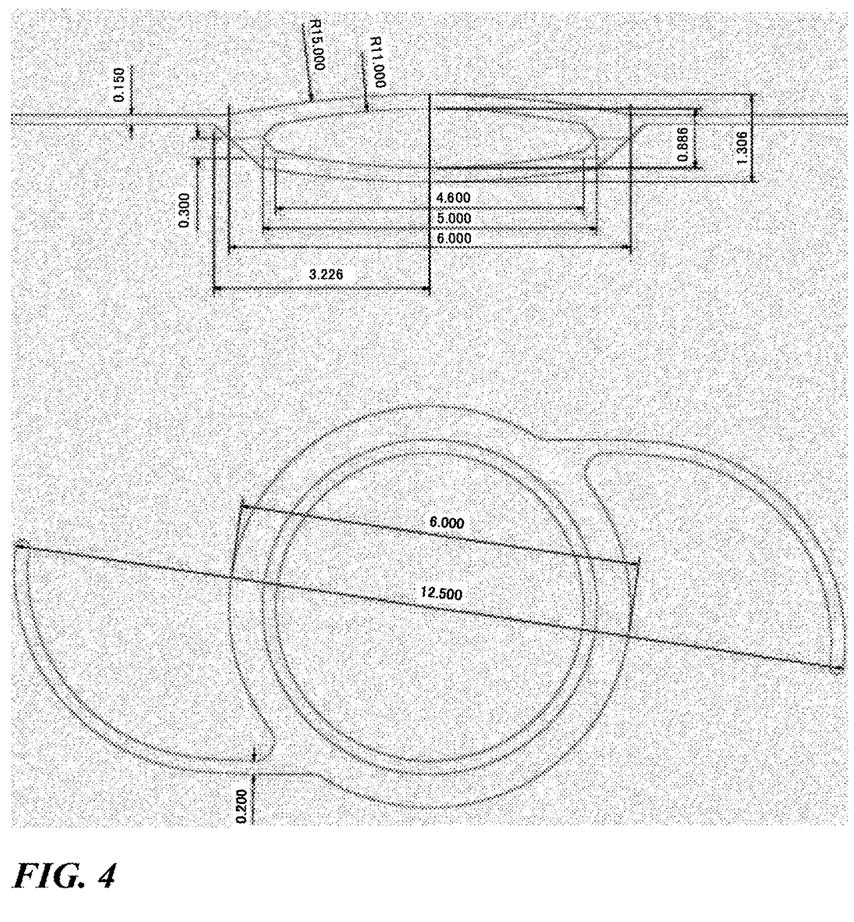
FIG. 4 is a design drawing of the PMMA hollow device.

In order to examine the drug release property, a 10% aqueous solution of sodium fluorescein as a low-molecular-weight water-soluble fluorescent dye was filled in the cavity of the PMMA hollow device and air-dried (FIG. 3(B)).

3. Enclosure of Intraocular Retention Gas and Transplantation into Rabbit

The solid fluorescein sodium-enclosed PMMA hollow device was placed in 100% $SF_6$ gas, and its hollow portion was filled with the gas (FIG. 3(B)). After a rabbit was anesthetized by intramuscular injection of Ketalar and Selactar, the pupil of the right eye was dilated with a 0.05% tropicamide•0.05% phenylephrine hydrochloride ophthalmic solution (Mydrin-P (registered trademark), Santen Pharmaceutical Co., Ltd.). The surgical field was disinfected and draped, the eyelid was opened with an eyelid opening device, and local anesthesia was performed with a 0.4% oxybuprocaine hydrochloride ophthalmic solution (Benoxil (registered trademark), Santen Pharmaceutical Co., Ltd.). After corneal puncture, the inside of the anterior chamber was replaced with a viscoelastic substance and anterior capsulotomy was performed with a bent 27 G needle. After that, the sclerocornea was incised by 2.4 mm, and the crystalline lens was removed by supersonic phacoemulsification and infusion & aspiration. Again, the inside of the anterior chamber was filled with the viscoelastic substance, and then the solid fluorescein sodium-enclosed PMMA hollow device whose cavity was filled with $SF_6$ gas was inserted into the capsule. The viscoelastic substance was removed, and the intraocular pressure was adjusted with a perfusion solution. An antibiotic eye ointment was applied to the conjunctival sac, and the operation was then completed.

4. Drug Release Test

Figure 5:
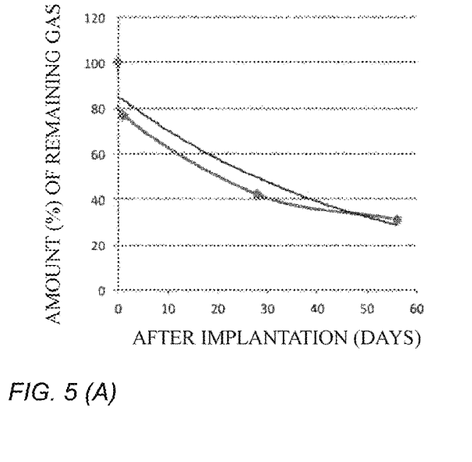

After surgery, the pupil was periodically dilated, the anterior ocular segment was photographed, and anterior chamber water was sucked and collected. The residual amount of gas was measured from the photograph of the anterior ocular segment and the content of fluorescein sodium in the anterior chamber water sample was measured with a fluorescence intensity meter. Not less than 30% of the $SF_6$ gas remained at the stage of 2 months. After initial burst, stable sustained release of the drug was observed from the first week (FIGS. 5(A) and (B)). In this manner, it was confirmed that the gas remained for 2 months or longer, and that a stable sustained drug release effect was achieved. Incidentally, the initial burst can be controlled by the design of the device (hollow device).

B. Examination 2 of Effectiveness of Sustained Drug Release System

1. Preparation of Drug-Containing Sustained Release Device and Enclosure of Drug•Intraocular Retention Gas The hollow device (FIGS. 6(A) and (B)) made of VisiJet (registered trademark) Crystal (ultraviolet curable acrylic resin) was produced by using a three-dimensional (3D) printer (Projet 3510HD plus). After filling the hollow device with a cetuximab solution as an antibody drug, it was subjected to freeze drying treatment. The properties of the sustained release device 10, which was produced in this manner and filled with cetuximab as a porous body, were investigated. Comparison was made between the case where air was used and the case where a sufficient amount of $SF_6$ was substituted for air ($SF_6$ enclosed), just before transplantation, as the gas to be filled in the device.

2. Transplantation into Rabbit

Figure 7:
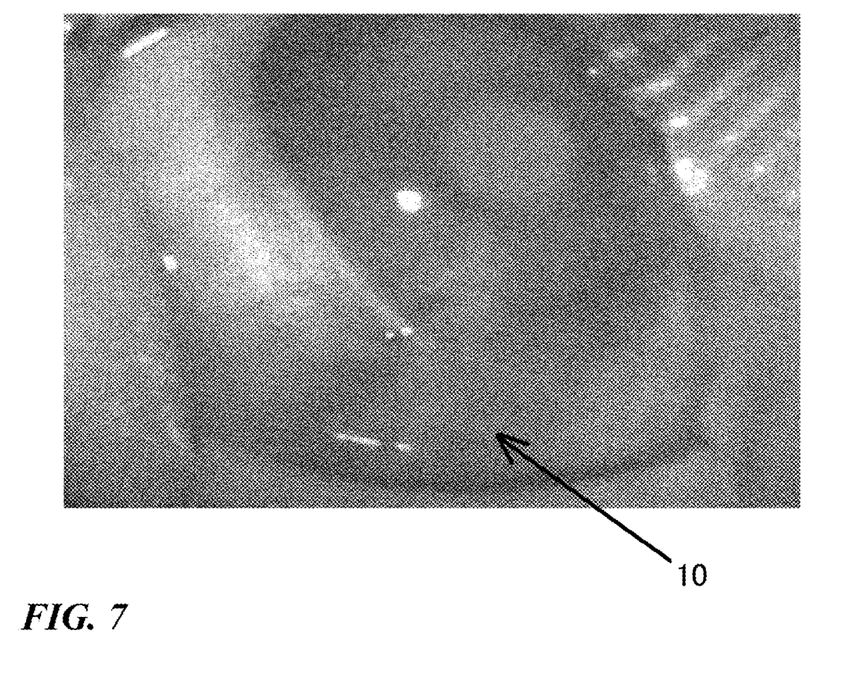
FIG. 7 is a view showing a state in which the sustained release device 10 is implanted extraocularly.

After a rabbit was anesthetized by intramuscular injection of Ketalar and Selactar, the pupil of the right eye was dilated with a 0.05% tropicamide•0.05% phenylephrine hydrochloride ophthalmic solution (Mydrin-P (registered trademark), Santen Pharmaceutical Co., Ltd.). Next, after surface anesthesia by ocular instillation of oxybuprocaine hydrochloride (Benoxil ophthalmic solution, Santen Pharmaceutical Co., Ltd.), the conjunctiva was incised to expose the sclera, and a sclerocornea tunnel was prepared. The tubular part was inserted into the sclerocornea tunnel and the sustained release device was implanted extraocularly so that the tip of the tubular part was positioned at the peripheral part of the anterior chamber (FIG. 7).

3. Drug Release Test

Figure 8:
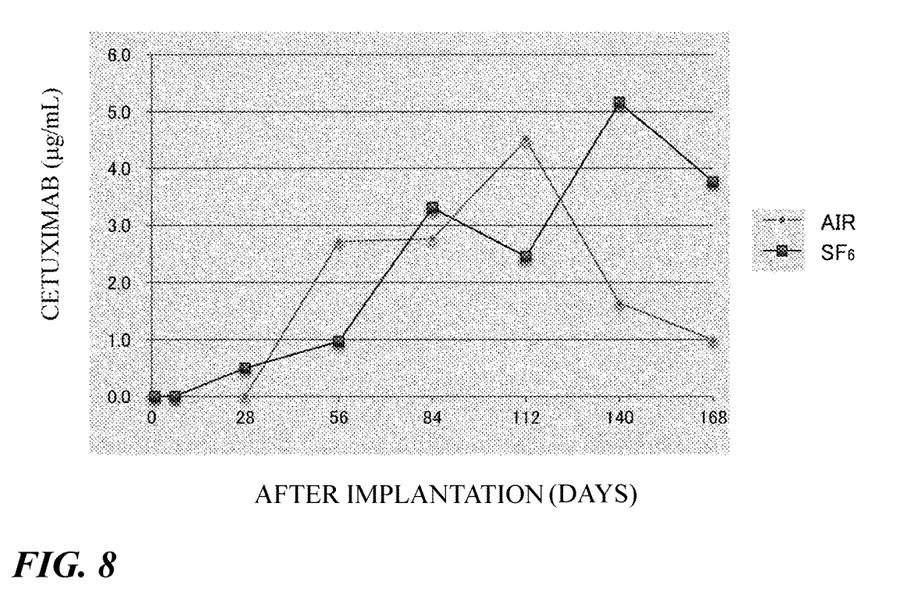
FIG. 8 shows a drug release profile of a cetuximab-containing sustained release device after transplantation into a rabbit.

After surgery, anterior chamber water was sucked and collected periodically, and cetuximab in the anterior chamber water sample was quantified with an ELISA kit. As a result, sustained release over 6 months or longer could be confirmed (FIG. 8). In addition, it was shown that the case where $SF_6$ was enclosed was more suitable for long-term sustained release than the case where air was enclosed.

INDUSTRIAL APPLICABILITY

The sustained release device of the present invention is used for treatment and prevention of eye diseases. The sustained release device of the present invention is useful for the sustained release of water-soluble, especially, polymer compounds, which has been difficult with the conventional drug release control system using a polymer.

The present invention is not limited to the description of the embodiments and example of the present invention at all. Various modifications that can be easily achieved by those skilled in the art without departing from the claims also fall within the scope of the invention. The contents of the articles, patent laid-open publications, patent publications, and the like specified herein shall be cited by incorporation in their entity.

REFERENCE SIGNS LIST

FIG. 1(A) to FIG. 1(H) Sustained release device
a Drug enclosing part
b Intraocular retention gas enclosing part
c Opening part
d Tubular part
w Partial partition wall
1 to 4 Transplantation site
10 Sustained release device
11 Opening part
12 Tubular part
13 Main body part

The invention claimed is:

1. A device for sustained release of an ophthalmic drug, consisting of:
   a single container, having one opening part, being filled with a plurality of drug enclosing parts in an alternating arrangement with a plurality of intraocular retention gas enclosing parts adjacent to the drug enclosing parts, wherein the drug enclosing parts are completely separated from each other by the intraocular retention gas enclosing parts and the intraocular retention gas enclosing parts are completely separated from each other by the drug enclosing parts, wherein prior to a release of any intraocular retention gas or the ophthalmic drug enclosed in one of the plurality of drug enclosing parts, one of the plurality of intraocular retention gas enclosing parts is adjacent to the one opening part, whereby in use in an eye the intraocular retention gas adjacent to the opening part is released, eliminating a sealing effect of the intraocular retention gas on one of the plurality of drug enclosing parts adjacent to the released intraocular retention gas, and an intraocular fluid can then reach the one of the plurality of drug enclosing parts, the drug enclosed in the one of the plurality of drug enclosing parts dissolves and diffuses to be released to an outside of the container, whereby another intraocular retention gas in alternating arrangement with and adjacent to the one of the plurality of drug enclosing parts is released eliminating the sealing effect of another intraocular retention gas on another one of the plurality of drug enclosing parts, and the intraocular fluid can then reach the another one of the plurality of drug enclosing parts, the drug enclosed in the another one of the plurality of drug enclosing parts dissolves and diffuses to be released to the outside of the container, whereby the sustained release of the drug continues until all of the plurality of drug enclosing parts are used up, and wherein the intraocular retention gas is composed of sulfur hexafluoride and/or propane octafluoride.

2. The device for sustained release of an ophthalmic drug according to claim 1,
wherein a plurality of units each comprising one pair of the drug enclosing part and the intraocular retention gas enclosing part are provided,
wherein the distance from the one opening part to the drug enclosing part is different among the units.

3. The device for sustained release of the ophthalmic drug according to claim 2, wherein the plurality of units are provided in series along a direction away from the one opening part.

4. The device for sustained release of the ophthalmic drug according to claim 2, wherein a volume of the intraocular retention gas enclosing part is different among the plurality of units.

5. A device for sustained release of an ophthalmic drug consisting of:
a single container, having one opening part, being filled with a plurality of drug enclosing parts in an alternating arrangement with a plurality of intraocular retention gas enclosing parts adjacent to the drug enclosing parts,
a plurality of units each comprising one pair of the drug enclosing part and the intraocular retention gas enclosing part are provided and a distance from the one opening part to the drug enclosing part is different among the units,
a plurality of partial partition walls are provided to partially partition the plurality of units,
wherein the drug enclosing parts are completely separated from each other by the intraocular retention gas enclosing parts and one of the plurality of partial partition walls, and the intraocular retention gas enclosing parts are completely separated from each other by the drug enclosing parts and one of the plurality of partial partition walls, wherein prior to a release of any intraocular retention gas or the ophthalmic drug enclosed in one of the plurality of drug enclosing parts, one of a plurality of intraocular retention gas enclosing parts is adjacent to the one opening part, whereby in use in an eye the intraocular retention gas adjacent to the opening part is released, eliminating a sealing effect of the intraocular retention gas on one of the plurality of drug enclosing parts adjacent to the released intraocular retention gas, and an intraocular fluid can then reach the one of the plurality of drug enclosing parts, the drug enclosed in the one of the plurality of drug enclosing parts dissolves and diffuses to be released to an outside of the container, whereby another intraocular retention gas in alternating arrangement with and adjacent to the one of the plurality of drug enclosing parts is released eliminating the sealing effect of another intraocular retention gas on another one of the plurality of drug enclosing parts, and the intraocular fluid can then reach the another one of the plurality of drug enclosing parts, the drug enclosed in the another one of the plurality of drug enclosing parts dissolves and diffuses to be released to the outside of the container, whereby the sustained release of the drug continues until all of the plurality of drug enclosing parts are used up, and wherein the intraocular retention gas is composed of sulfur hexafluoride and/or propane octafluoride.

6. The device for sustained release of the ophthalmic drug according to claim 1, wherein the container is made of a material having permeability of the intraocular retention gas and biocompatibility.

7. The device for sustained release of the ophthalmic drug according to claim 6, wherein the material is an acrylic resin, glass, Ti, a Ti alloy, or an Ni alloy.

8. The device for sustained release of the ophthalmic drug according to claim 1, wherein the drug enclosed in the drug enclosing part is water-soluble.

9. The device for sustained release of the ophthalmic drug according to claim 1, wherein the drug is enclosed, in a liquid or solid state, in the drug enclosing part.

10. A device for sustained release of an ophthalmic drug, consisting of:
a single container, having a plurality of opening parts, being filled with a plurality of drug enclosing parts in an alternating arrangement with a plurality of intraocular retention gas enclosing parts adjacent to the drug enclosing parts,
a plurality of units each comprising one pair of the drug enclosing part and the intraocular retention gas enclosing part are provided,
a plurality of partition walls are provided to partition the plurality of units, and
each of the plurality of units has one opening part of the plurality of opening parts,
wherein prior to a release of any intraocular retention gas or a drug enclosed in one of the plurality of drug enclosing parts, each one of a plurality of intraocular retention gas enclosing parts is adjacent to one opening part of the plurality of opening parts,
whereby in use in an eye the intraocular retention gas adjacent to the opening part of one of the plurality of units is released, eliminating a sealing effect of the intraocular retention gas on one of the plurality of drug enclosing parts adjacent to the released intraocular retention gas, and an intraocular fluid can then reach the one of the plurality of drug enclosing parts, the drug enclosed in the one of the plurality of drug enclosing parts dissolves and diffuses to be released to an outside of the container, whereby another intraocular retention gas is released eliminating the sealing effect of another intraocular retention gas on another one of the plurality of drug enclosing parts, and the intraocular fluid can then reach the another one of the plurality of drug enclosing parts, the drug enclosed in the another one of the plurality of drug enclosing parts dissolves and diffuses to be released to the outside of the container, whereby the sustained release of the drug continues until all of the plurality of drug enclosing parts are used up, and wherein the intraocular retention gas is composed of sulfur hexafluoride and/or propane octafluoride.

11. A device for sustained release of an ophthalmic drug consisting of:
- a single container, having one opening part, being filled with a plurality of drug enclosing parts and an intraocular retention gas enclosing part adjacent to the drug enclosing parts,
- a plurality of partial partition walls are provided to partition the plurality of drug enclosing parts,
- wherein the drug enclosing parts are completely separated from each other by one of the plurality of partial partition walls, and the intraocular retention gas enclosing part is adjacent to all of the plurality of drug enclosing parts,
- wherein prior to a release of any intraocular retention gas or the ophthalmic drug enclosed in one of the plurality of drug enclosing parts, the intraocular retention gas enclosing part is adjacent to the one opening part,
- whereby in use in an eye the intraocular retention gas adjacent to the opening part is released, eliminating a sealing effect of the intraocular retention gas on the plurality of drug enclosing parts adjacent to the released intraocular retention gas, and an intraocular fluid can then reach the one of the plurality of drug enclosing parts, the drug enclosed in the one of the plurality of drug enclosing parts dissolves and diffuses to be released to an outside of the container, whereby the intraocular fluid can then reach the another one of the plurality of drug enclosing parts, the drug enclosed in the another one of the plurality of drug enclosing parts dissolves and diffuses to be released to the outside of the container, whereby the sustained release of the drug continues until all of the plurality of drug enclosing parts are used up, and
- wherein the intraocular retention gas is composed of sulfur hexafluoride and/or propane octafluoride.

12. The device for sustained release of the ophthalmic drug according to claim 5, wherein the plurality of units are provided in series along a direction away from the one opening part.

13. The device for sustained release of the ophthalmic drug according to claim 5, wherein a volume of the intraocular retention gas enclosing part is different among the plurality of units.

14. The device for sustained release of the ophthalmic drug according to claim 5, wherein the container is made of a material having permeability of the intraocular retention gas and biocompatibility.

15. The device for sustained release of the ophthalmic drug according to claim 10, wherein the container is made of a material having permeability of the intraocular retention gas and biocompatibility.

16. The device for sustained release of the ophthalmic drug according to claim 11, wherein the container is made of a material having permeability of the intraocular retention gas and biocompatibility.

17. The device for sustained release of the ophthalmic drug according to claim 14, wherein the material is an acrylic resin, glass, Ti, a Ti alloy, or an Ni alloy.

18. The device for sustained release of the ophthalmic drug according to claim 15, wherein the material is an acrylic resin, glass, Ti, a Ti alloy, or an Ni alloy.

19. The device for sustained release of the ophthalmic drug according to claim 16, wherein the material is an acrylic resin, glass, Ti, a Ti alloy, or an Ni alloy.

* * * * *